(12) United States Patent
Cline

(10) Patent No.: US 8,096,980 B2
(45) Date of Patent: Jan. 17, 2012

(54) CONTROLLED EVACUATION OSTOMY DEVICE WITH EXTERNAL SEAL

(75) Inventor: John B. Cline, New Brunswick, NJ (US)

(73) Assignee: ConvaTec Technologies Inc., Las Vegas, NV (US)

( * ) Notice: Subject to any disclaimer, the term of this patent is extended or adjusted under 35 U.S.C. 154(b) by 0 days.

(21) Appl. No.: 11/430,542

(22) Filed: May 9, 2006

(65) Prior Publication Data
US 2006/0206069 A1    Sep. 14, 2006

Related U.S. Application Data

(60) Division of application No. 10/811,055, filed on Mar. 26, 2004, which is a continuation of application No. 10/107,998, filed on Mar. 27, 2002, now Pat. No. 6,723,079.

(51) Int. Cl.
*A61F 5/44* (2006.01)

(52) U.S. Cl. ........ 604/332; 604/277; 604/333; 604/334; 604/335; 604/336; 604/337; 604/338; 604/339; 604/340; 604/341; 604/342; 604/343; 604/344; 604/345; 604/355; 600/30; 600/31; 600/32; 128/887

(58) Field of Classification Search .......... 604/277, 604/332–345, 355; 600/30–32; 128/887
See application file for complete search history.

(56) References Cited

U.S. PATENT DOCUMENTS

| 543,400 | A | * | 7/1895 | Ormerod | 128/887 |
| 2,324,520 | A | * | 7/1943 | Lamson | 600/32 |
| 2,520,831 | A | | 8/1950 | Chincholl | |
| 2,563,597 | A | | 8/1951 | Friedman | |
| 2,765,790 | A | | 10/1956 | Dickson | |
| 3,052,236 | A | * | 9/1962 | Schrieber | 602/13 |
| 3,071,133 | A | * | 1/1963 | Eisen | 602/13 |
| 3,543,744 | A | * | 12/1970 | Lepar | 600/435 |
| 3,581,732 | A | | 6/1971 | Ruiz | |
| 4,096,853 | A | * | 6/1978 | Weigand | 600/431 |
| 4,121,589 | A | * | 10/1978 | McDonnell | 604/328 |
| 4,233,977 | A | * | 11/1980 | Mattson | 604/335 |

(Continued)

FOREIGN PATENT DOCUMENTS

EP    1 348 411 A1 *    10/2003

(Continued)

OTHER PUBLICATIONS stoma. (2008). In Merriam-Webster Online Dictionary. Retrieved Jun. 3, 2008, from http://www.merriam-webster.com/dictionary/stoma.*

(Continued)

*Primary Examiner* — Tatyana Zalukaeva
*Assistant Examiner* — Ilya Treyger
(74) *Attorney, Agent, or Firm* — Stuart E. Krieger

(57) ABSTRACT

A flexible membrane is situated within a rigid or semi-rigid cap. The edge of the cap wall is adhesively fixed to the tissue surrounding the stoma. The interior of the cap is pressurized to press the membrane to seal the stoma against the discharge of solid and semi-solid waste. Gas escapes through a vent with a filter element. The cap can be pressurized by an external pump or an integral pump member situated on top of the cap. A relief valve prevents over pressurization. A collection pouch can be provided as part of a device. The device can be removably mounted on a standard two-piece faceplate.

11 Claims, 10 Drawing Sheets

U.S. PATENT DOCUMENTS

| | | | | |
|---|---|---|---|---|
| 4,381,765 A | * | 5/1983 | Burton | 600/32 |
| 4,596,566 A | * | 6/1986 | Kay | 604/343 |
| 4,662,890 A | * | 5/1987 | Burton | 623/1.31 |
| 4,721,508 A | * | 1/1988 | Burton | 604/338 |
| 4,723,952 A | * | 2/1988 | Esposito | 604/338 |
| 4,775,374 A | * | 10/1988 | Cilento et al. | 604/344 |
| 4,950,223 A | * | 8/1990 | Silvanov | 600/32 |
| 5,195,996 A | * | 3/1993 | Edwards et al. | 604/338 |
| 5,261,898 A | * | 11/1993 | Polin et al. | 604/328 |
| 5,366,478 A | * | 11/1994 | Brinkerhoff et al. | 606/213 |
| 5,433,724 A | * | 7/1995 | Kawasaki et al. | 606/202 |
| 5,569,216 A | * | 10/1996 | Kim | 604/277 |
| 5,795,314 A | * | 8/1998 | Berenstein | 601/166 |
| 6,508,794 B1 | * | 1/2003 | Palumbo et al. | 604/317 |
| 6,520,943 B1 | * | 2/2003 | Wagner | 604/338 |
| 6,689,111 B2 | * | 2/2004 | Mulhauser et al. | 604/332 |
| 6,723,079 B2 | * | 4/2004 | Cline | 604/337 |

FOREIGN PATENT DOCUMENTS

| | | |
|---|---|---|
| EP | 1 348 412 A1 * | 10/2003 |
| GB | 751333 | 9/1954 |
| GB | 751333 * | 6/1956 |
| WO | WO 92/18074 A1 * | 10/1992 |

OTHER PUBLICATIONS

MedicineNet.com, definition of stoma, www.medterms.com.*
MedicineNet.com, definition of ostomy, www.medterms.com.*

* cited by examiner

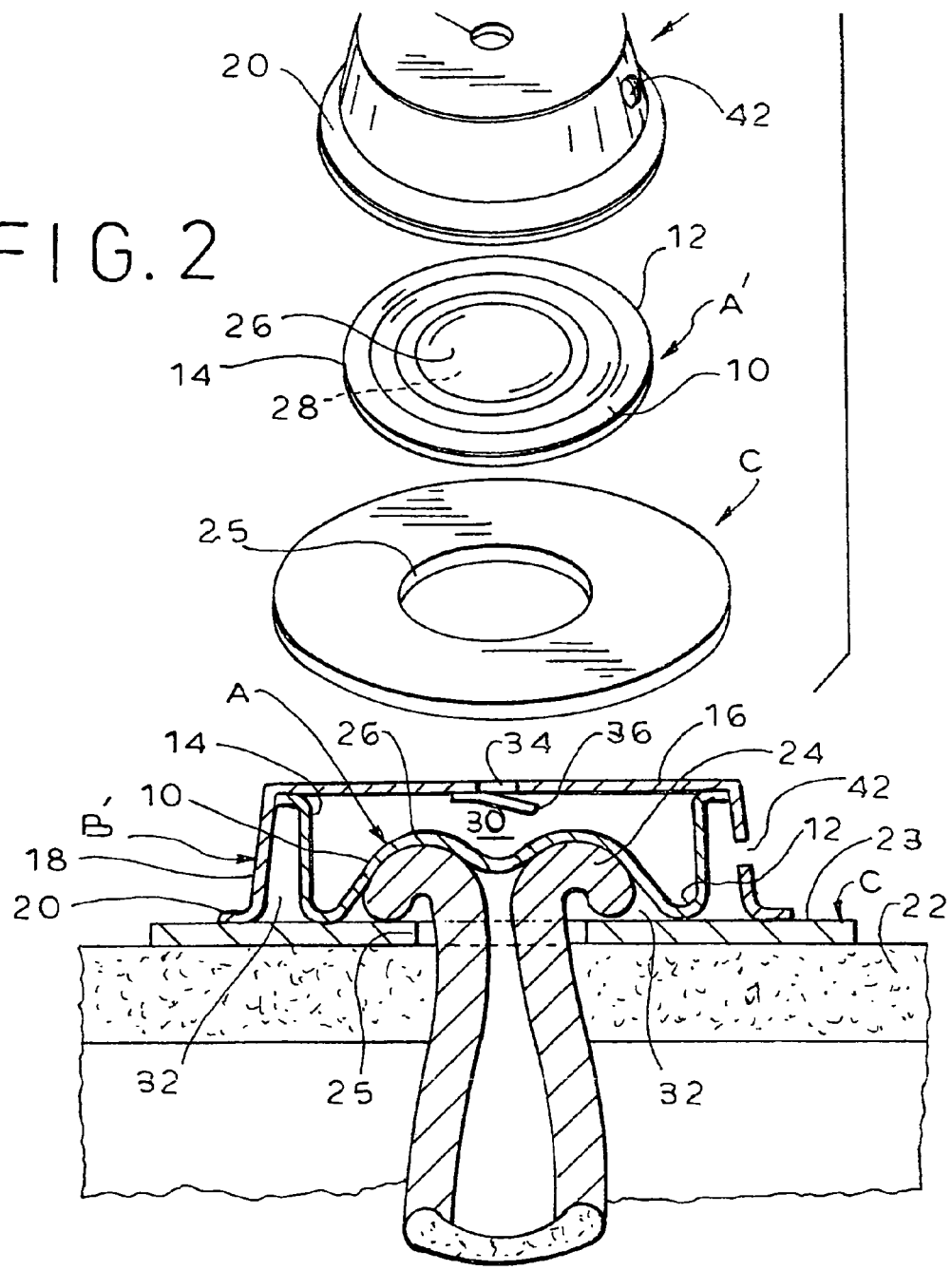

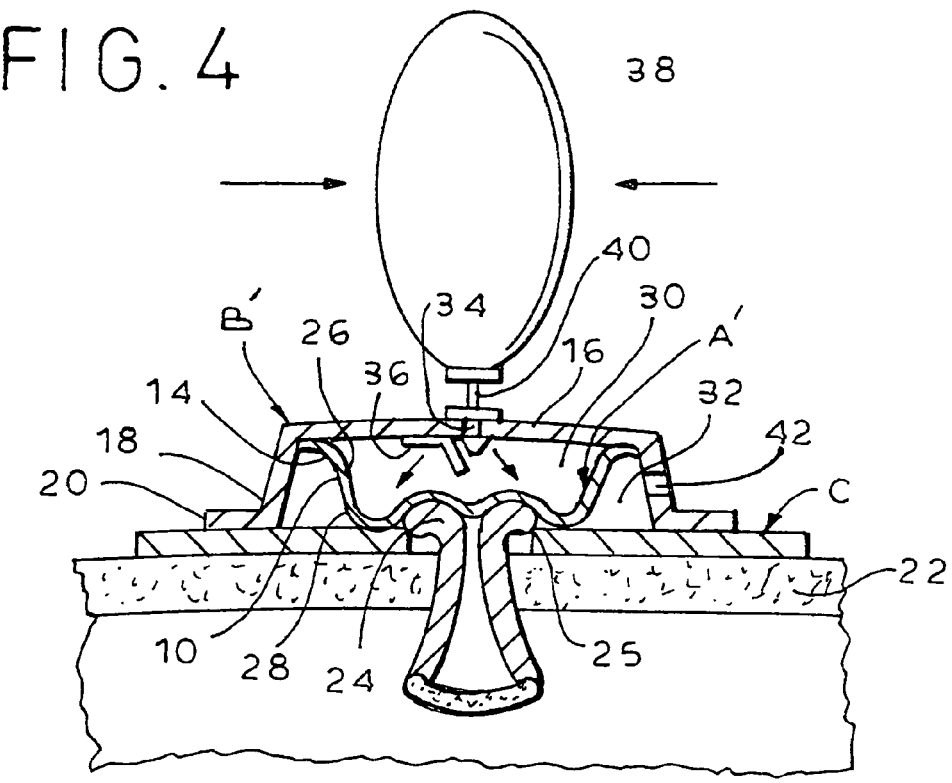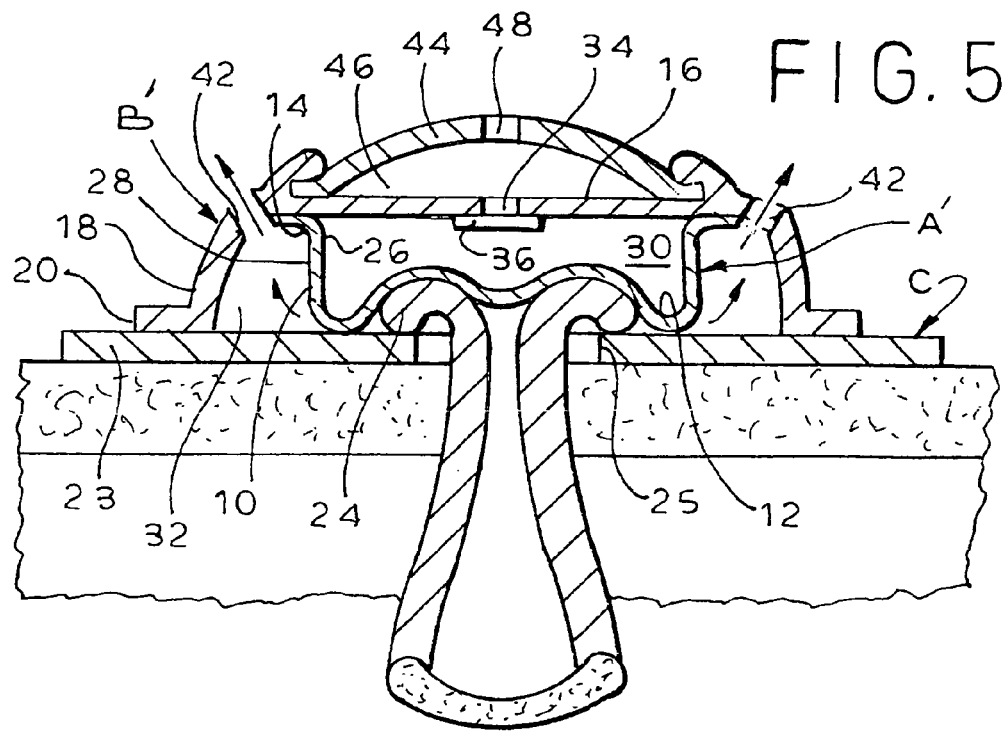

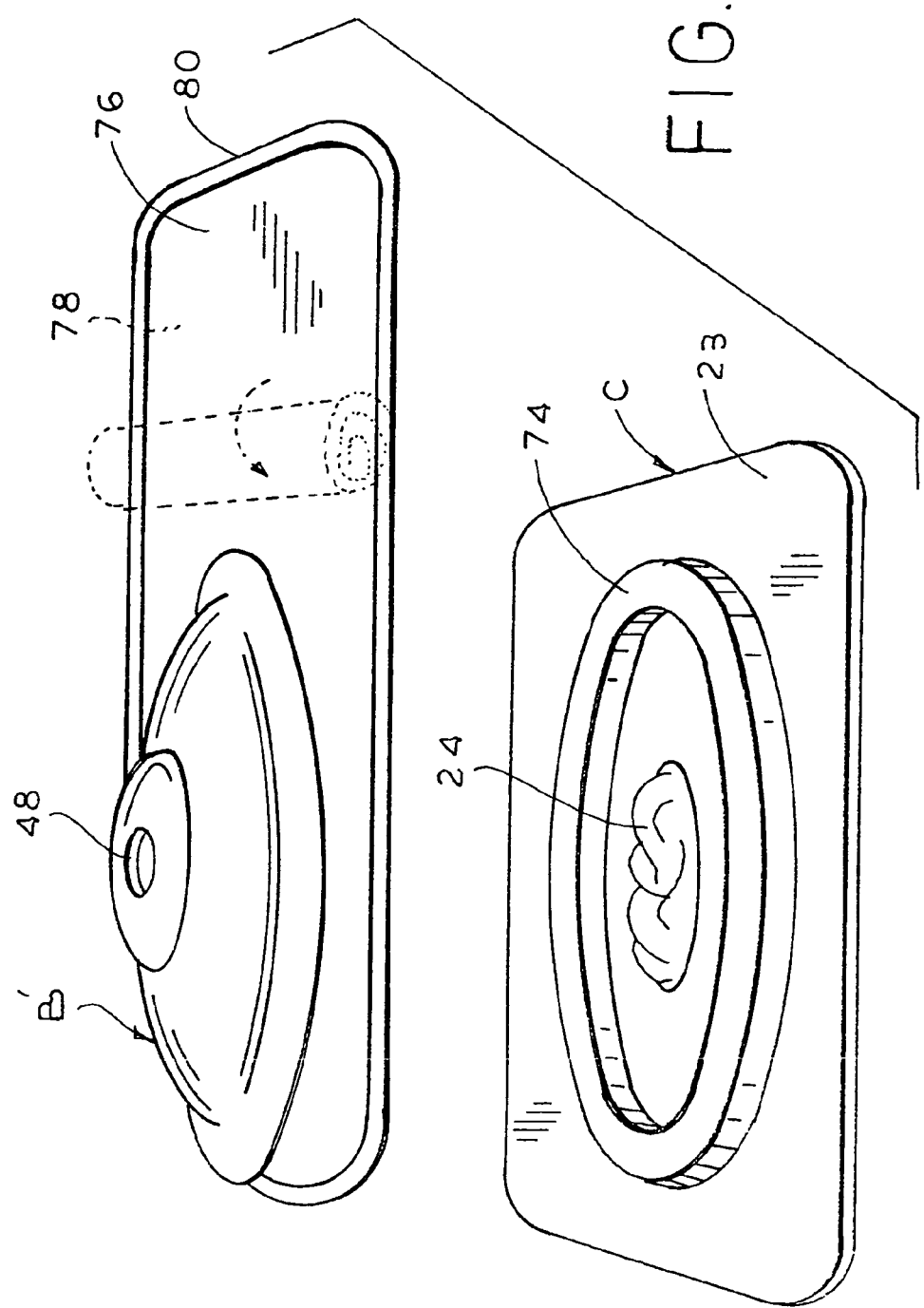

CONTROLLED EVACUATION OSTOMY DEVICE WITH EXTERNAL SEAL

CROSS-REFERENCE TO RELATED APPLICATIONS

This application is a divisional of application Ser. No. 10/811,055 filed Mar. 26, 2004 which is a continuation of application Ser. No. 10/107,998 filed Mar. 27, 2002, now U.S. Pat. No. 6,723,079.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION (1) Field of the Invention

The present invention relates to ostomy devices of the type adapted to be adhesively affixed to the skin surrounding the stoma and more particularly to such a device which includes external means for controlling evacuation by sealing the stoma while exerting only a minimum amount of sealing pressure.

Certain surgical procedures known as colostomy, ileostomy and urostomy result in an opening in the abdominal wall, called a stoma, which permits waste discharge from the interior of a body cavity. Since the patient has no control over the waste discharge, it is often necessary for the patients who have undergone these surgical procedures to utilize an ostomy device to protect the stoma and collect the waste material as it is discharged.

Over the years, ostomy devices of a variety of different types and constructions have been utilized. Various materials and adhesives have been developed to increase the utility and wareability of the devices.

(2) Description of Related Art

The basic ostomy device includes a collection receptacle or pouch connected to an adhesive coated faceplate which serves to mount the pouch to the body. The pouch includes first and second thin film walls which are sealed by heat welding or the like along the periphery. The pouch has an inlet opening designed to be aligned with the stoma and an outlet for emptying material from the pouch. In single piece devices, the pouch is permanently affixed to the adhesive coated faceplate. In two piece devices, the pouch is detachably mounted to the faceplate by coupling rings or the like, permitting the pouch to be replaced without removal of the faceplate each time.

The two piece device requires a means for releasably mounting the pouch to the faceplate. One particularly successful structure takes the form of a pair of annular or ring-like rigid or semi-rigid plastic parts, one in the form of an axially extending rib and the other in the form of a channel into which the rib may be removably received and frictionally engaged.

These ostomy devices collect waste as it is discharged but include no means for controlling when discharge takes place. One of the main objectives of these devices is to increase the freedom of mobility of the wearer and thus the wearer's ability to lead a normal life by participating in various activities. However, having discharge take place into the collection pouch in certain situations may cause embarrassment to the wearer because of the noise or smell or because of the increase in the size of the pouch.

Accordingly, it is desirable to control when evacuation takes place so that it does not occur at times which may cause embarrassment. Since the patient has no means to control waste discharge, it is desirable to provide a mechanical means by which waste discharge can be managed. One way to do this is to temporarily seal the stoma opening so as to prevent discharge when the seal is present. Once the seal is removed, evacuation of the bowel can take place.

However, an important concern in the management of stomas is to avoid exerting excess local pressure on the mucosal tissue. High local pressure can damage the stoma. Further, it can prevent blood flow to the tissue if the applied pressure exceeds capillary pressure. Thus, any acceptable evacuation control device must seal the stoma exerting harmful pressure on the stoma or surrounding tissue.

BRIEF SUMMARY OF THE INVENTION

The seal, which forms the subject of the invention, is designed to be mounted externally and to exert a low pressures (preferably between 10 mm Hg and 30 mm Hg) across the entire face of the stoma. The seal itself is formed of a thin and flexible membrane. The membrane is preferably made of a material with good barrier properties. One possible candidate material is the film used in the manufacture of ostomy pouches. Under a minimal amount of external pressure, the membrance drapes itself across and around the stoma, covering most surface irregularities. Based on preliminary laboratory test results, the device can prevent release of stool from the bowel with internal bowel pressure of 50 mm Hg and above.

Such a seal would adapt itself to a variety of stoma sizes and shapes. It would also be, by design, a slightly "imperfect" seal, so that it would block the release of solid or semi-solid matter but would allow gas to escape. The ability of the seal to permit gas to escape is important to the management of waste in the bowel, since at any given time more than two-thirds of the volume in the bowel is gas. Releasing gas in a controlled way minimizes discomfort and maximizes the time between evacuations.

The tissue surrounding the stoma may be very sensitive. It is therefore also important that only minimal activation pressure be required to create the seal.

Further, it is desirable that the sealing device be interchangeable with a standard two-piece ostomy device collection pouch. In this way, the sealing device can be coupled to a standard two-piece ostomy device collection pouch. In this way, the sealing device can be coupled to a standard two-piece ostomy device faceplate, eliminating the necessity of removing an appliance that is adhesively attached to the skin after each evacuation and hence the damage to the skin inherent in such repeated removals.

It is, therefore, a prime object of the present invention to provide a controlled evacuation ostomy device which includes an external seal.

It is another object of the present invention to provide a controlled evacuation ostomy device with an external seal which exerts a minimum amount of sealing pressure on the mucosal tissue.

It is another object of the present invention to provide a controlled evacuation ostomy device with an external seal which permits the release of gas from the bowel while preventing the discharge of solid or semi-solid materials.

It is another object of the present invention to provide a controlled evacuation ostomy device with an external seal which requires minimum pressure to create the seal.

It is another object of the present invention to provide a controlled evacuation ostomy device with an external seal which is compatible with standard two-piece ostomy devices.

In accordance with one aspect of the present invention, an ostomy device is provided including a thin, flexible membrane. Means are provided for securing the membrane to the tissue surrounding the stoma. Means are also provided for pressing the membrane against the stoma to seal the stoma.

The membrane has an edge. The securing means includes an adhesive layer on the membrane edge.

The pressing means includes a member situated over and sealed to the membrane. The member and the membrane define an internal chamber. The chamber can be pressurized to press the membrane against the stoma. Means are provided for pressurizing the internal chamber.

In accordance with another aspect of the present invention, an ostomy device is provided including a member formed of a wall with an edge. Means are provided for adhering the edge of the wall to the tissue surrounding the stoma. Sealing means are situated within member, proximate the stoma. The sealing means has a first surface and a second surface. The sealing means defines a chamber within the member interior, between its first surface and the wall. The chamber can be pressurized to press the second surface of the sealing means against the stoma.

The sealing means comprises a flexible membrane. The membrane has an edge. The membrane edge is fixed to the interior surface of the member. The membrane also preferably includes one or more circumferential pleats.

The device includes means for pressurizing the chamber. The pressurizing means includes means in the member wall for permitting the entrance of fluid, such as air, into the chamber. The entrance means includes an inlet port and a one way valve.

The pressurizing means may include an external pump device. Alternatively, it may include a pump device integral with the member.

The integral pump device includes a flexible wall affixed to the member. The flexible wall defines a chamber external to the member. The volume of the external chamber can be reduced by the application of pressure on the flexible wall. The entrance port connects the external pump cavity and the internal chamber of the member.

Means are provided for limiting the pressure introduced into the internal chamber of the member. The pressure limiting means includes a pressure relief valve.

The sealing means defines a second internal chamber between its second surface and the member wall. Means are provided for venting the second internal chamber. The venting means includes an outlet port.

The venting means may also include gas filtration means. The filtration means includes a filter element operatively imposed between the second internal chamber and the outlet port. Any one of a variety of activated carbon filter formulations and constructions, including the use of protective microporous membranes, can be considered appropriate for use in this regard.

The member wall edge sealing means includes means for engaging the edge of the member wall and means for adhering the edge engaging means to the tissue surrounding the stoma. The edge engaging means may include means for removeably engaging the edge of the member.

The device may be designed for use in combination with waste collection means, such as a waste collection pouch. The waste collection means is situated between the member wall and the edge sealing means. The waste collection means may be collapsible, preferably with a concertina-like configuration.

The waste collection means may include a collection pouch with first and second flexible walls sealed around the periphery. The walls are fixed between the member and the edge sealing means, respectively.

The collection pouch may be elongated. Means for storing the pouch proximate the member may be provided.

BRIEF DESCRIPTION OF THE SEVERAL VIEWS OF THE DRAWINGS

To these and such other objects which may hereinafter appear, the present invention relates to a controlled evacuation ostomy device with an external seal, as set forth in the following specification and recited in the annexed claims, taken together with the accompanying drawings, wherein like numerals refer to like parts, and in which:

FIG. 2 is an exploded view of the cap member, sealing membrane and adhering means of a first preferred embodiment of the ostomy device of the present invention;

FIG. 3 is a side cross-sectional view of a first preferred embodiment of the present invention, as it would appear mounted over a stoma and pressurized.

FIG. 4 is a side cross-sectional view of the embodiment of FIG. 3, with an external pump in place;

FIG. 5 is a side cross-sectional view of a second preferred embodiment of the present invention, as it would appear mounted over a stoma and pressurized;

FIG. 15 is an exploded isometric view of the embodiment of the invention shown in FIG. 13, showing the pouch in extended position and, in phantom, in the rolled position.

DETAILED DESCRIPTION OF THE INVENTION

Figure 1:
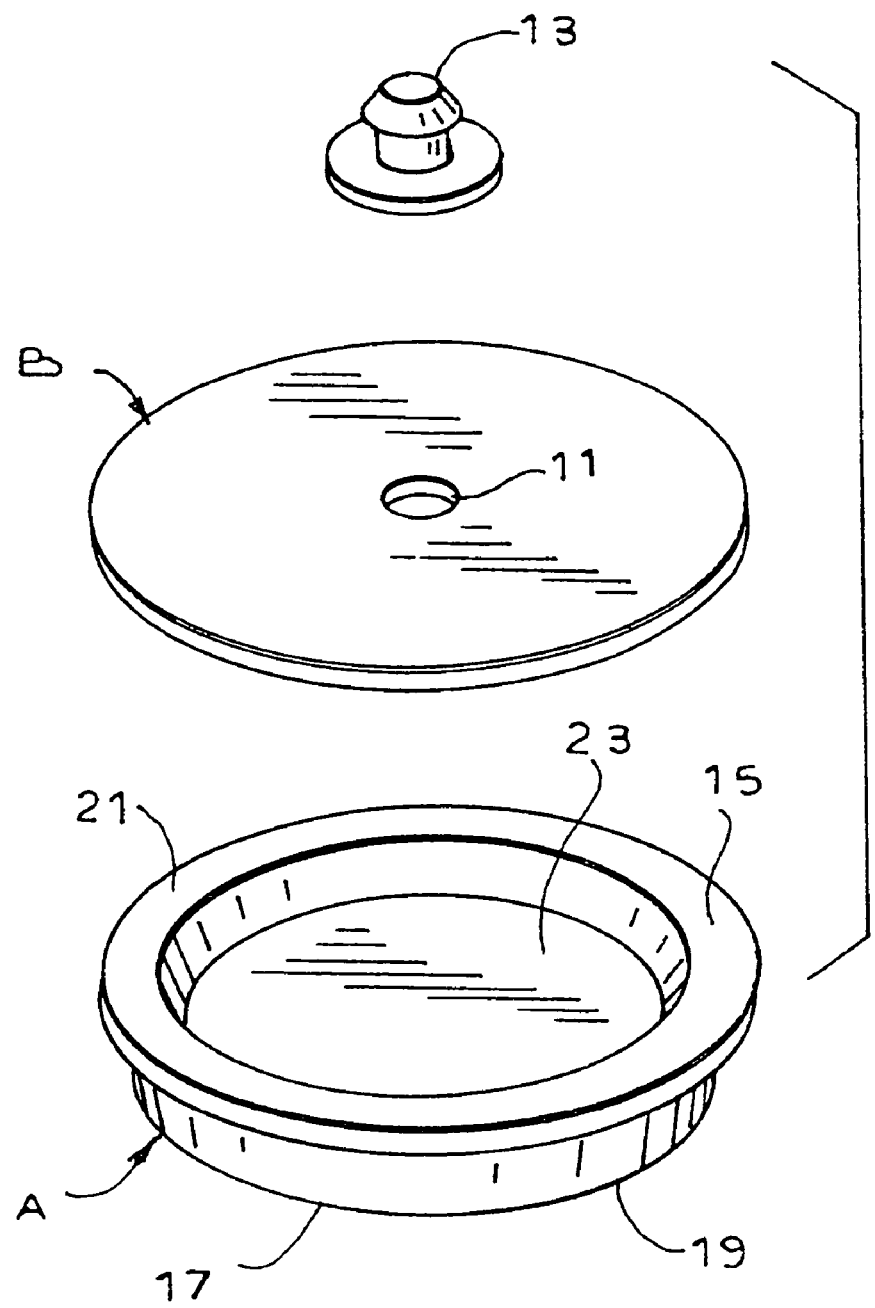
FIG. 1 is an exploded view of the device of the present invention in its simplest form.

As illustrated in FIG. 1, the present invention in its simplest form comprises a thin, flexible membrane, generally designated A and a disc-like cover member, generally designated B. Member B includes a port 11. A plug 13 is provided to seal port 11.

Membrane A has a cup shape with a closed bottom and an outwardly extending top flange 15. A layer of adhesive 17 is situated on the rim 19 of the bottom of the membrane to seal the membrane to the tissue surrounding the stoma.

A second layer 21 of adhesive is placed on flange 15 so as to seal member B to flange 15. Between membrane A and member B is a defined internal chamber 23.

Chamber 23 is pressurized by forcing air or other fluid through port 11. This can be accomplished by using an external pump device, not shown in this figure. Once the chamber is pressurized to the desired degree, the port is sealed by plug 13. The pressure within the chamber causes membrane A to press against the stoma to seal the stoma opening.

As seen in FIGS. 2-4, the first preferred embodiment of the present invention includes a flexible sealing membrane generally designated A' adapted to cover and seal the stoma. Sealing membrane A' is situated within a cap-like member, generally designated B', which surrounds member A'. Cap member B' is temporarily affixed to the tissue surrounding the stoma by an adhesive means, generally designed C.

Sealing member A' is preferably a round, thin, flexible membrane 10 with circumferential pleats 12. The edge 14 of member 10 is fixed to the undersurface of the top wall 16 of cap B'. Cap B' is made of rigid or semi-rigid material. Cap B' has a generally cylindrical sidewall 18 with an outwardly extending flange 20 extending from its bottom edge.

Although sealing membrane A' is shown as a round thin, flexible membrane or diaphragm, it can be of any shape. Illustrated is one preferred shape, that of a "rolling diaphragm", in which one or more circumferential pleats 12 are formed. The pleats allow the seal to be stored in a small space, allow it to adjust to different stoma heights, and also allow it to be "presented" to the face of the stoma in an optimal way for pressurization.

Membrane 10 can be made of a variety of thin, flexible plastic films. An ideal film would be thin, flexible, and possess good barrier properties. One such film would be a film used to fabricate ostomy pouches, although a wide variety of films could be utilized.

Cap B' is temporarily attached to the skin around the stoma by adhesive means C, preferably coated on the underside of a flexible wafer used in conventional ostomy devices and known as a faceplate. The adhesive can be any skin compatible adhesive, many different formulations of which are known in the art.

Thus, flange 20 of cap B' is adhesively attached to the upper surface of faceplate 23. Faceplate 23 is temporarily attached to the tissue 22 surrounding the stoma 24 by the adhesive coating on the undersurface of faceplate 23. Faceplate 23 has a central opening 25 through which the stoma extends.

Membrane 10 has a top surface 26 and a bottom surface 28. As best seen in FIG. 3, membrane 10 divides the interior of cap B' into two chambers. The first chamber 30 is defined between the top surface 26 of the membrane and the undersurface of the top wall 16 of the cap. The second chamber 32 is defined between the bottom surface 28 of the membrane, on the one hand, and the upper surface of faceplate 23 and interior surface of sidewall 18 of the cap, on the other hand.

Top wall 16 of cap B' is provided with an entrance port 34. One side of a flap 36 is fixed to the underside of top wall 16, proximate port 34, and functions as a one-way or "check" valve. The check valve could have any one of several embodiments, including "duckbill", flap, or an "umbrella" valve configuration.

As seen in FIG. 4, an external hand pump 38 with a flexible bulb of conventional design may be used to pressurize chamber 30, and thus press membrane 10 against the stoma. Pump 38 has a nozzle 40 designed to be inserted in port 34. Removal of nozzle 40 from port 34 permits flap 36 to seal the port.

The seal created by the membrane 10 is, by design, not a perfect seal. Slight irregularities in the face of the stoma and/or slight wrinkles that form in the seal material create very small leak paths. In practice, these leak paths are too small for solid or semi-solid stool to pass, but allow any flatus that is present at the face of the seal to be released. Since as much as two-thirds of the volume of the bowel is comprised of flatus, release of flatus is important with respect to user comfort and maximizing the time between evacuations.

Once flatus has been released past the seal, it is preferable for it to be deodorized by means of a filtration element, as described below. For example, an activated carbon filter identical to those used in ostomy pouches may be used for this purpose.

Vent port 42 is formed through cap sidewall 18 connecting chamber 32 with the exterior of the cap. Gas released from the stoma into chamber 32 due to the irregularities in membrane 10 is routed through port 42 to the cap exterior.

Another way to pressurize the seal is by means of a flexible diaphragm pump built into the cap member itself as illustrated in FIG. 5. The integral pump would also incorporate a check valve 36 to prevent air from escaping from the seal. This could also be accomplished by a non-return valve similar to, but much smaller than, the non-return valve built into a typical urostomy pouch.

As seen in FIG. 5, the integral pump can take the form of a dome-like flexible part 44 fixed over top wall 16, defining a variable volume chamber 46. An opening 48 is formed through part 44, proximate the top thereof. To pressurize chamber 30, the user places his or her finger over opening 48 and presses downwardly on part 44 decreasing the volume of chamber 46 and forcing air through port 34. The finger is then removed, allowing part 44 to return to its original position, as chamber 46 again fills with air. This action is repeated until sufficient pressure is built up in chamber 30 to seal membrane 10 over the stoma.

Limiting the pressure applied to the seal is an important concern, as noted previously. One objective of the present invention is to ensure that sealing pressure exerted on the bowel or stoma does not exceed local capillary pressure, to prevent necrosis of mucosal tissue. The device therefore preferably includes a pressure relief valve that will open at pressures exceeding a pre-set limit. An elastomeric "umbrella" valve can be employed for this purpose, but a variety of other relief valve configurations could be used, including a spring-loaded disc, a spring-loaded poppet, or a flexible membrane.

Figure 6:
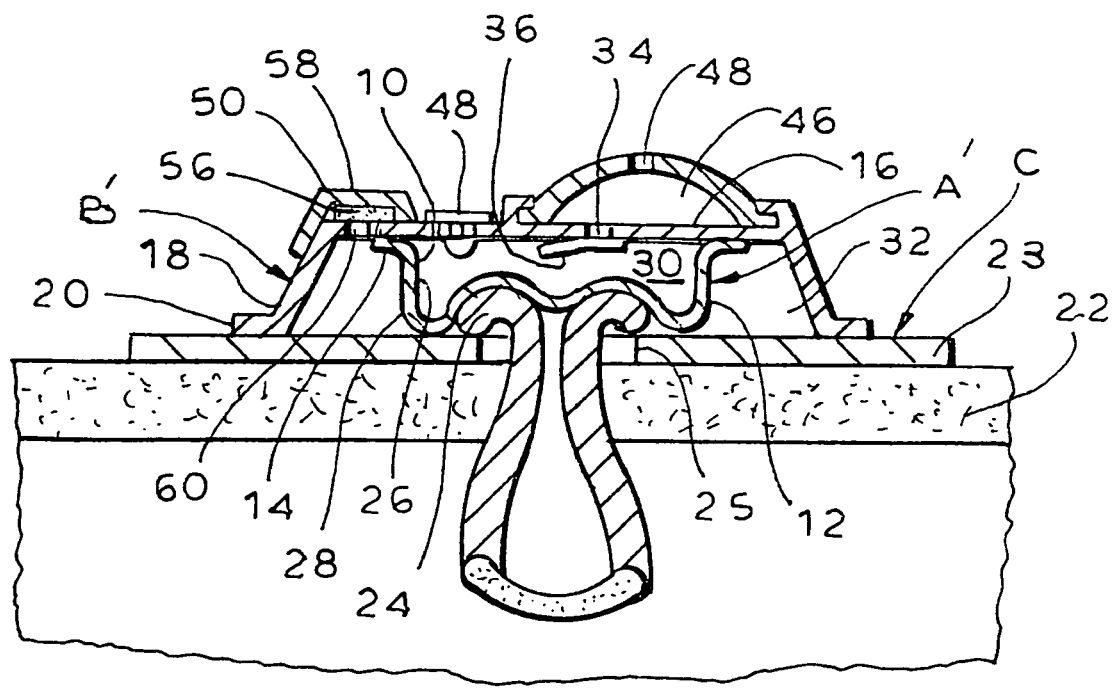
FIG. 6 is a side cross-sectional view of a third preferred embodiment of the present invention, as it would appear mounted over a stoma and pressurized.
Figure 7:
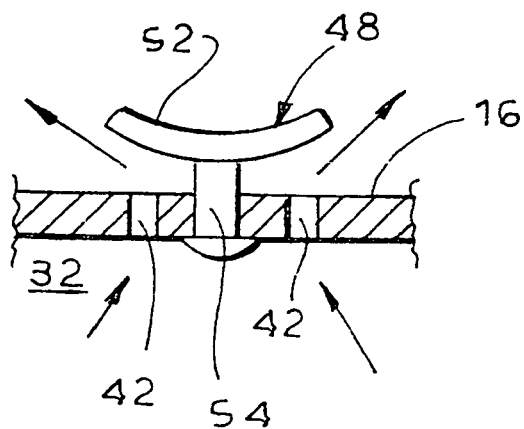
FIG. 7 is an enlarged view of a pressure relief valve.

The preferred embodiment of FIG. 6 includes a somewhat smaller integral pump, similar in structure to the dome of FIG. 5, so as to provide room in the cap top for a pressure relief valve 48 and a gas filter 50. FIG. 7 illustrates the structure of a preferred embodiment of the relief valve 48, which has an "umbrella" like configuration. It consists of a flap 52 fixed to the cap by a stem 54. Flap 52 normally covers the vent ports 42 in the top of the cap. Flap 52 is formed to have sufficient rigidity to prevent air from venting from chamber 30 until the air pressure in chamber 30 exceeds a predetermined pressure.

Figure 9:
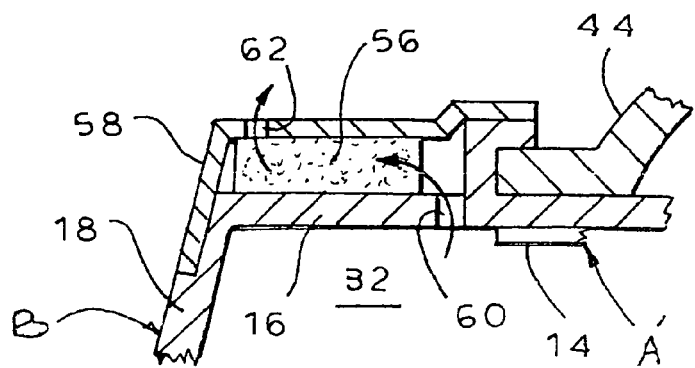
FIG. 9 is an enlarged cross-sectional view of a portion of the embodiment of FIG. 8, showing the gas filtration member.

Filter 50, as best seen in FIG. 9, consists of a filter element 56, which may be formed of activated charcoal or any other filter material. The filter element is situated in housing 58 interposed between port 60 on the top wall 16 of cap B' and an exit port 62 in the top of housing 58.

Figure 8:
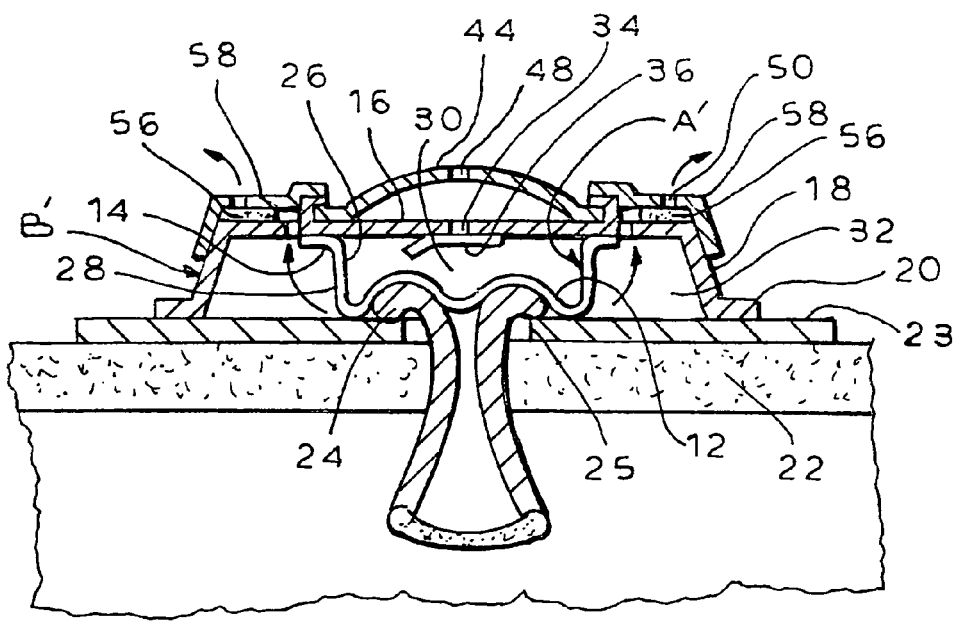
FIG. 8 is a side cross-sectional view of a fourth preferred embodiment of the present invention, as it would appear mounted over a stoma and pressurized.

FIG. 8 illustrates another preferred embodiment, similar to that of FIG. 6, except that integral pump dome part 44 is centrally located on the cap top and a second filter 56 is provided for increased venting.

Cap B' can be attached directly to the skin surrounding the stoma using a temporary adhesive similar to the adhesives used to attach a one-piece ostomy pouch to the skin, as illustrated in FIG. 1. Another means of attachment is to affix the cap to a faceplate attached to the skin, as illustrated in FIGS. 2-6 and 8. Still another method is to engage the cap to a standard two-piece ostomy faceplate, as illustrated in FIGS. 10, 11, 13 and 15. In those embodiments, the cap is preferably connected to the faceplate in the same manner as a two-piece ostomy pouch. It would be interchangeable with two-piece ostomy pouches, so that the user would have the option at any time to use the controlled evacuation device or a standard ostomy pouch, without the necessity of removing the faceplate.

Figure 10:
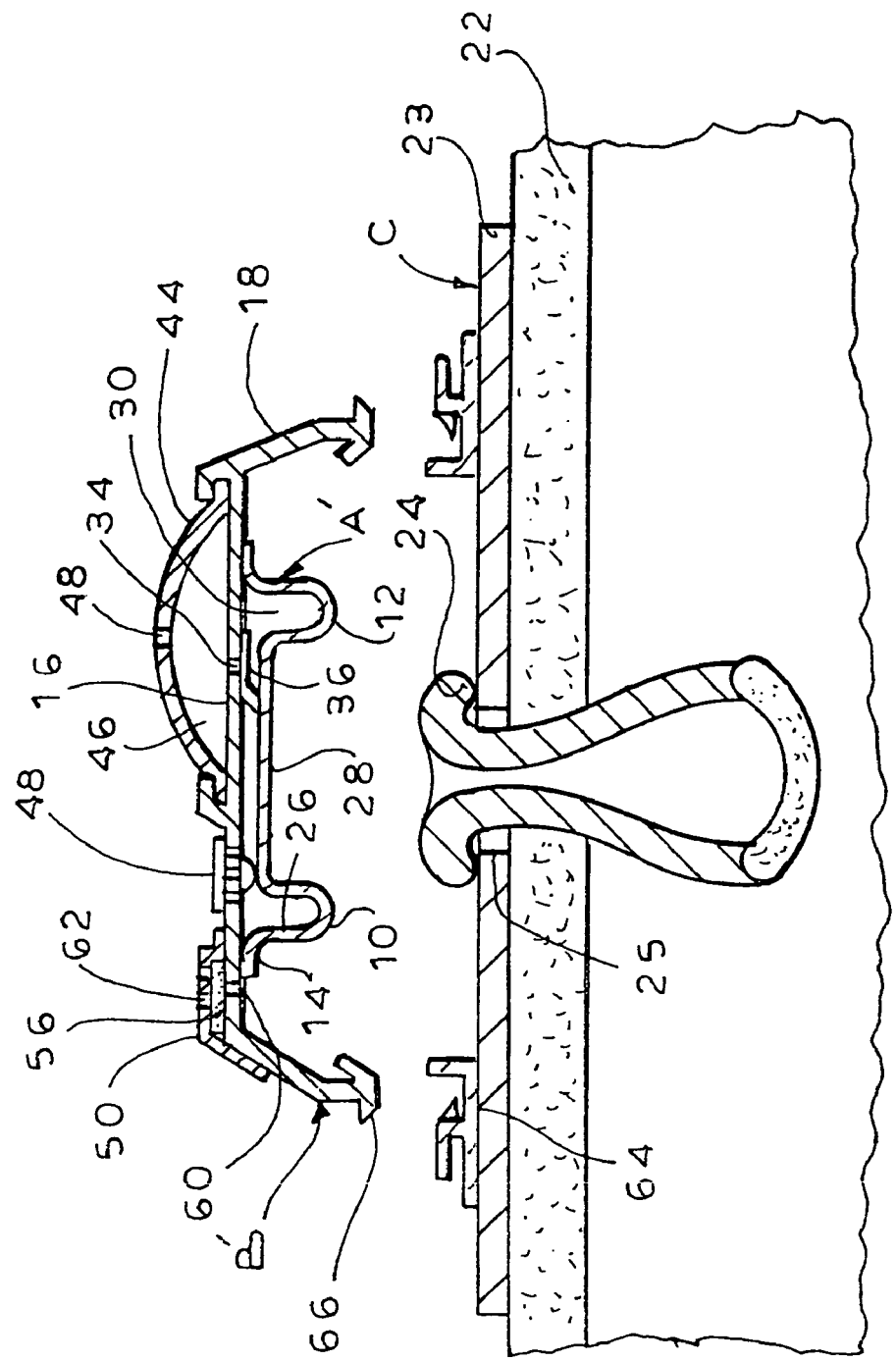
FIG. 10 is an exploded cross-sectional view of a fifth preferred embodiment of the present invention.

FIG. 10 illustrates a preferred embodiment, similar to that of FIG. 6, except that cap B' and faceplate 23 are provided with interengaging parts such that the cap can be removed from the body without detaching the faceplate.

In this embodiment, faceplate 23 is provided with an annular channel 64 permanently attached to its exterior surface. Flange 20, which formed the bottom edge of cap side wall 18 in previous embodiments, is replaced with an annular protrusion or ring 66 which is adapted to be removably received in channel 64. The exterior surface of ring 66 and the interior surface of channel 64 are provided with interlocking flexible parts, well known in the art, to insure that the ring is received within the channel in a manner which creates a gas-tight seal. This method of attaching the device to the wafer can be extended to other embodiments employing coupling means of a variety of configurations.

When the membrane seal is removed from the stoma, the contents of the bowel will be evacuated and must be collected and disposed of. One means of facilitating collection and disposal is to incorporate a collection pouch into the controlled evacuation device.

One possible pouch configuration would be a cylindrically shaped membrane made of thin flexible plastic film, concentric with the center axis of the device. Such a membrane would be collapsed into a thin annular space for storage in the device. When evacuation is required, the user would detach the cap from the device, leaving a base component still attached to the ostomy faceplate. One end of the member would be attached to the cap, the other end to the base component. Removal of the cap would expand the pouch, much like the bellows of a concertina. Once the contents of the bowel are released to the pouch, the base component would also be removed from the faceplate and the entire device would be disposed of in a suitable refuse container.

Figure 11:
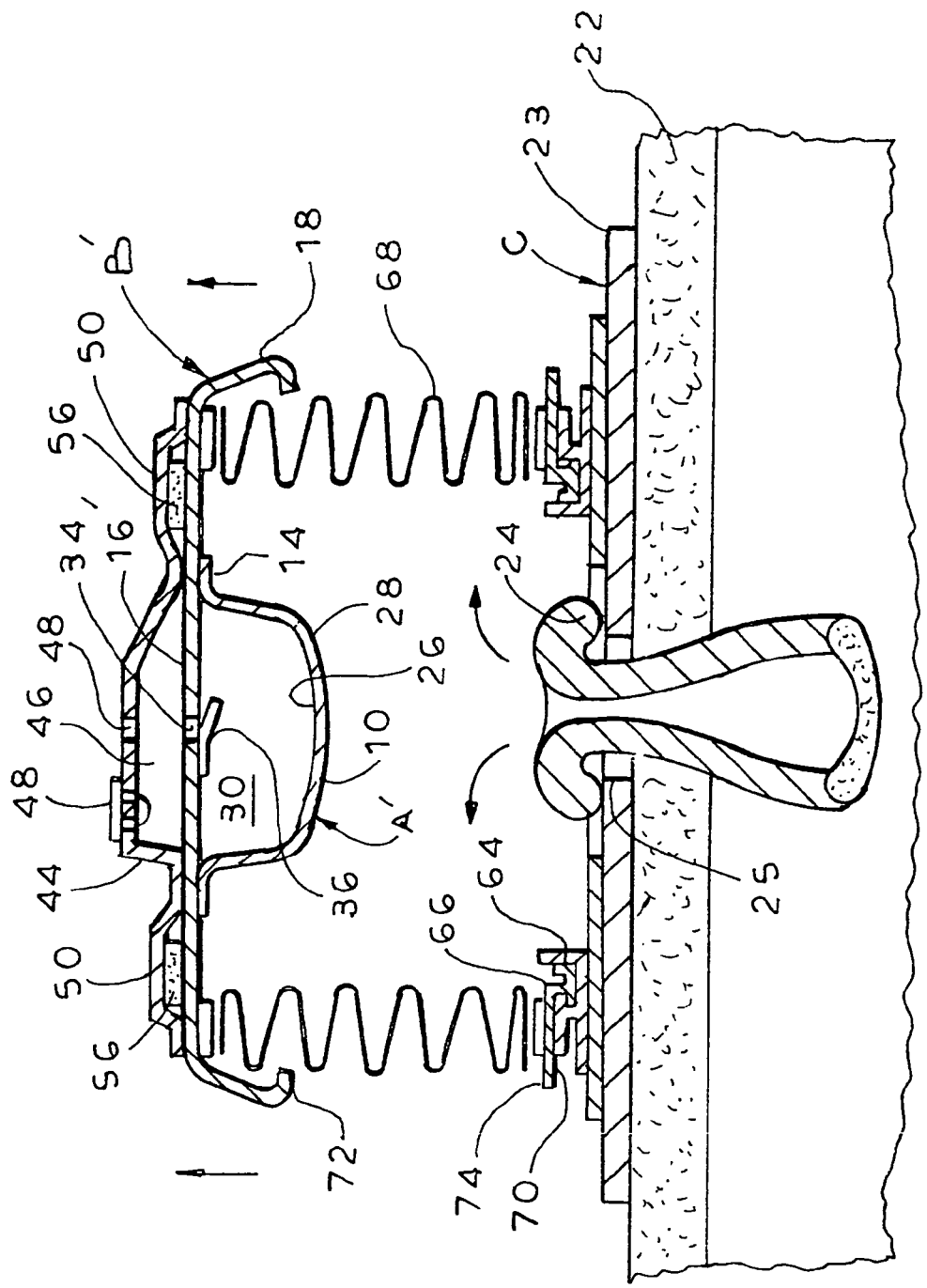
FIG. 11 is an exploded cross-sectional view of a sixth preferred embodiment of the present invention.

This is illustrated in FIG. 11. That figure shows a preferred embodiment of the present invention that is similar to that of FIG. 10 in that the cap is detachable from the faceplate, but differs in that it incorporates a thin walled collection pouch 68. Pouch 68 is generally cylindrical with openings at each end. One end of pouch 68 is attached to the underside of the top wall 18 of cap B'. The other end of pouch 68 is affixed to an annular base member 70 which carries engaging ring 66. As before, ring 66 is detachably received in channel 64 fixed to the exterior surface of faceplate 23.

Figure 12:
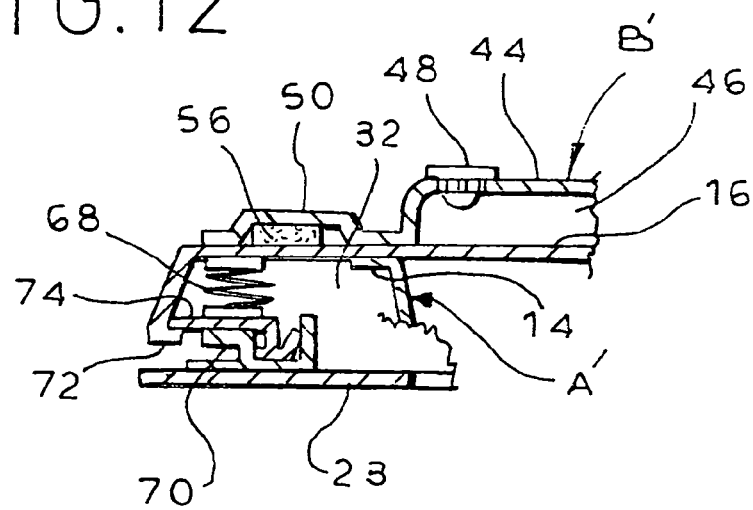
FIG. 12 is a cross-sectional view of a portion of the embodiment of FIG. 11 showing the collection pouch in the contracted state.

Wall 18 of cap B' is provided with an inwardly directed flange 72 which is designed to lodge under an outwardly directed lip 74 which forms part of base member 70. While pressurized, cap B' sits on base member 70, with flange 72 under lip 74. The wall of pouch 68 is collapsed like a concertina, as seen in FIG. 12. When evacuation is to take place, flange 72 is removed from under lip 74, cap B' is moved away from faceplate 23, unsealing the stoma and expanding the pouch as the bowel is evacuated into the pouch. Base member 70 is then detached from faceplate 23 and the cap/pouch/base assembly is disposed of. Other means of removably attaching cap B' to the base are possible, including a variety of snap-fit designs, frangible seals, "tear off" seals, and adhesive.

Other collection pouch configurations are also possible, including a long, narrow sleeve-type pouch made of thin plastic film. One of the pouch panels would be attached to the base component, the other panel would be attached to the cap. The cap would snap onto the base component as before. The pouch could be rolled tightly up onto itself, much like a bedroll, and stored adjacent to the cap.

When the user evacuates, the pouch would unroll or unfold from the base component, and the pouch would fill with effluent. Once the pouch is full, the base component would be removed from the faceplate and the entire device disposed of in an appropriate receptacle.

It would be possible to configure the cap to cover the pouch so that it would not be visible until the cap is removed. In this embodiment, the cap could be molded in a soft material that would not adversely affect the comfort of the user.

Figure 14:
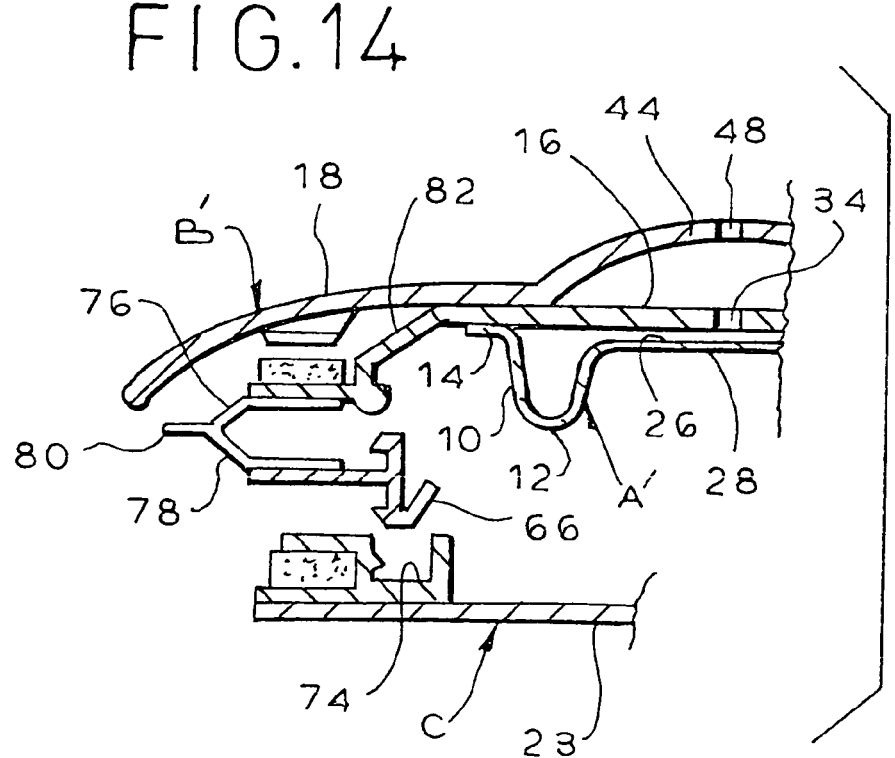
FIG. 14 is a side cross-sectional view of a portion of the embodiment of FIG. 13 with the cap/pouch member detached from the faceplate.
Figure 13:
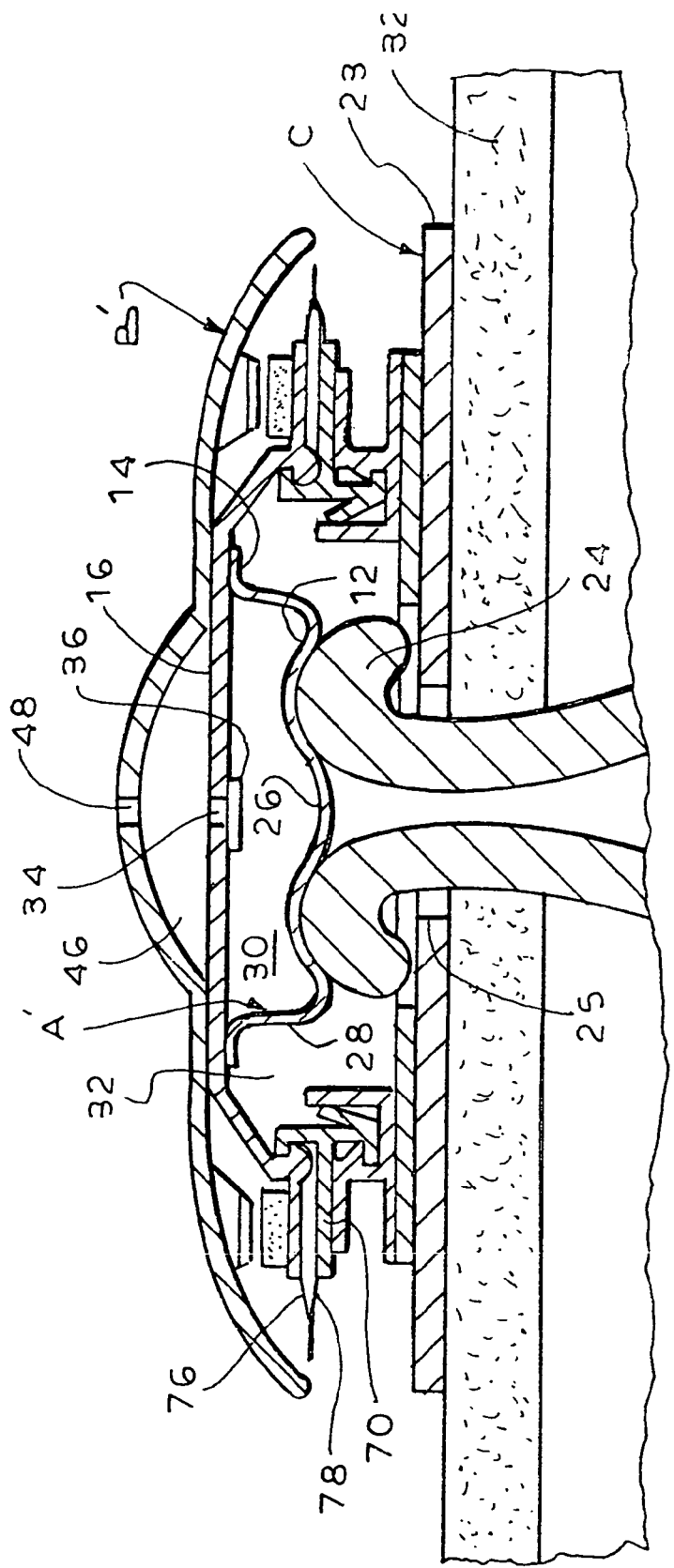
FIG. 13 is a side cross-sectional view of a seventh preferred embodiment of the present invention, as it would appear mounted over a stoma and pressurized.

FIGS. 13, 14 and 15 illustrate another preferred embodiment of the present invention in which the collection pouch takes an elongated form, similar to a conventional collection pouch. The collection pouch is formed of top and bottom thin flexible walls 76, 78 heat sealed to each other around the periphery 80. Each wall has a circular opening.

The portion of pouch wall 76 around the opening therein is fixed to a part 82, which is an extension of top wall 16 of cap B'. The portion of pouch wall 78 around the opening therein is affixed to base 70, which carries engaging ring 66, which in turn is detachably received in channel 64 on faceplate 23. When the device is in the sealed condition, the collection pouch is rolled up and retained proximate the cap, as seen in phantom in FIG. 14.

When the seal is released, the pouch is unrolled and discharge is collected. Ring 66 of base 70 is then detached from channel 64 on faceplate 23, as seen in FIG. 14, and the cap/pouch/base assembly is discarded. The faceplate remains in place and a new cap/pouch/base assembly is mounted and pressurized to seal the stoma.

It will now be appreciated that the present invention relates to an ostomy device which employs an external seal to control evacuation. The seal is created by pressurizing a thin flexible membrane which covers the stoma. The seal exerts a minimum of pressure on the tissue surrounding the stoma and is activated without the application of force sufficient to damage sensitive tissue or cause discomfort. Several embodiments are disclosed, including devices with integral pumps, relief valves, gas filters and integral collection pouches of cylindrical and elongated configurations.

While only a limited number of preferred embodiments of the present invention have been disclosed for purposes of illustration, it is obvious that many modifications and variations could be made thereto. It is intended to cover all of the modifications and variations which fall within the scope of the present invention, as defined by the following claims:

I claim:

1. An ostomy device for sealing a stoma surgically formed in the abdominal wall created as a result of a colostomy, ileostomy or a urostomy so as to control the discharge of waste through the stoma, said device being situated entirely externally to the body and comprising flexible means, a rigid or semi-ridged member having an interior surface and an edge portion, and adhesive means for securing said edge portion of said member to the skin surrounding the stoma with said flexible means aligned and in direct contact with said stoma, said flexible means being fixed to said interior surface of said member to define a pressurizable chamber within said member, said flexible means being pressed against the stoma when said chamber is pressurized to prevent the passage of waste through the stoma.

2. The device of claim 1 wherein said flexible means and said member define a second chamber within said member.

3. The device of claim 2 further comprising means for venting said second chamber.

4. The device of claim 1 further comprising a fluid entrance port in said member connected to said pressurizable chamber.

5. The device of claim 4 further comprising means for pressurizing said chamber through said fluid entrance port.

6. The device of claim 5 wherein said pressurizing means comprises an external chamber connectible to said fluid entrance port the volume of which can be reduced by the application of pressure.

7. The device of claim 6 further comprising means for limiting the pressure in said pressurizable chamber.

8. The device of claim 7 wherein said pressure limiting means comprises a pressure relief valve.

9. The device of claim 1 further comprising waste collection means connected between said member and said adhering means.

10. The device of claim 9 wherein said waste collection means comprises a collection pouch.

11. The device of claim 9 wherein said waste collection means is collapsible.

* * * * *